(12) United States Patent
Williams et al.

(10) Patent No.: US 9,550,277 B1
(45) Date of Patent: Jan. 24, 2017

(54) ALIGNMENT AND ADJUSTMENT CLAMP

(71) Applicants: Matthew E. Williams, New York, NY (US); Brian D. Goldmark, Miami, FL (US)

(72) Inventors: Matthew E. Williams, New York, NY (US); Brian D. Goldmark, Miami, FL (US)

(*) Notice: Subject to any disclaimer, the term of this patent is extended or adjusted under 35 U.S.C. 154(b) by 0 days.

(21) Appl. No.: 14/517,068

(22) Filed: Oct. 17, 2014

(51) Int. Cl.
*B25B 27/14* (2006.01)
*B25B 5/10* (2006.01)
*B25B 5/16* (2006.01)
*A61B 17/28* (2006.01)
*B25B 5/12* (2006.01)
*B25B 5/00* (2006.01)

(52) U.S. Cl.
CPC ............. *B25B 5/10* (2013.01); *A61B 17/2812* (2013.01); *B25B 5/00* (2013.01); *B25B 5/12* (2013.01); *B25B 5/163* (2013.01)

(58) Field of Classification Search
USPC .......................................................... 29/271
See application file for complete search history.

(56) References Cited

U.S. PATENT DOCUMENTS

| | | | |
|---|---|---|---|
| 298,872 A | 5/1884 | May | |
| 603,975 A | 5/1889 | Schmitt | |
| 1,011,597 A | 12/1911 | Fischler | |
| 2,427,128 A | 9/1947 | Ettinger | |
| 2,502,804 A | 4/1950 | Spencer | |
| 2,583,896 A | 1/1952 | Siebrandt | |
| 2,617,458 A | 11/1952 | Kelly | |
| 3,269,230 A | 8/1966 | Cambron | |
| 3,646,939 A | 3/1972 | Sklar | |
| 3,754,331 A | 8/1973 | Agnone | |
| 3,807,718 A | 4/1974 | Sendoykas | |
| 4,369,788 A * | 1/1983 | Goald | A61B 17/1608 600/564 |
| 4,747,588 A * | 5/1988 | Dillhoff | B25B 5/12 269/258 |
| 4,896,661 A * | 1/1990 | Bogert | A61B 17/2812 600/219 |
| 4,950,273 A * | 8/1990 | Briggs | A61B 17/2833 30/251 |
| 4,994,024 A * | 2/1991 | Falk | A61B 17/1608 600/565 |
| 5,297,538 A * | 3/1994 | Daniel | A61B 17/0206 600/206 |
| 5,529,571 A * | 6/1996 | Daniel | A61B 17/0206 403/90 |
| 5,662,676 A * | 9/1997 | Konincky | A61B 17/0218 600/210 |
| 5,690,640 A | 11/1997 | Gotfried | |
| 5,931,777 A * | 8/1999 | Sava | A61B 17/02 600/210 |
| 5,993,385 A * | 11/1999 | Johnston | A61B 17/0206 600/213 |
| 6,042,540 A * | 3/2000 | Johnston | A61B 17/0206 600/213 |

(Continued)

*Primary Examiner* — Alvin Grant
(74) *Attorney, Agent, or Firm* — Middleton Reutlinger

(57) ABSTRACT

The present invention comprises an improved clamp for securing two members together. The invention includes a pair of clamp jaws that may be positioned in spaced relation to each another and adjusted in three dimensions.

4 Claims, 15 Drawing Sheets

(56) References Cited

U.S. PATENT DOCUMENTS

| | | | |
|---|---|---|---|
| 6,196,969 B1* | 3/2001 | Bester | A61B 17/0206 600/219 |
| 6,347,565 B2* | 2/2002 | Steinweg | 81/319 |
| 6,663,562 B2* | 12/2003 | Chang | A61B 17/0206 600/213 |
| 6,716,218 B2* | 4/2004 | Holmes | A61B 17/8866 606/105 |
| 6,860,179 B2* | 3/2005 | Hopper | B25B 5/06 81/318 |
| 7,104,166 B1 | 9/2006 | Wong | |
| 7,415,912 B2* | 8/2008 | Tyler | B25B 5/163 81/367 |
| 7,625,391 B2 | 12/2009 | Kebel et al. | |
| 7,749,231 B2* | 7/2010 | Bonvallet | A61B 17/025 606/90 |
| 7,842,045 B2* | 11/2010 | Vandenbroek | A61B 17/128 606/142 |
| 8,747,410 B2* | 6/2014 | Claypool | A61B 17/158 606/102 |
| 8,979,866 B2* | 3/2015 | Patel | A61B 17/025 606/105 |
| 8,979,891 B2* | 3/2015 | McLawhorn | A61B 17/08 606/142 |
| 2005/0251183 A1* | 11/2005 | Buckman | A61B 17/08 606/157 |
| 2009/0062869 A1 | 3/2009 | Claverie et al. | |
| 2013/0116733 A1 | 5/2013 | Stoll, Jr. | |
| 2014/0031882 A1 | 1/2014 | Schmuck et al. | |

\* cited by examiner

US 9,550,277 B1

ALIGNMENT AND ADJUSTMENT CLAMP

BACKGROUND OF THE INVENTION

Field of the Invention

The present invention relates generally to a clamp and more particularly to an improved clamp that is capable of securing two spaced members having a lateral offset and/or vertical offset from each other, thereby permitting multi-planar adjustment.

Description of the Related Art

Clamps of various designs and configurations are well known in the art. Prior art clamps are used in myriad applications, including woodworking, plumbing, general construction, metal working, and surgeries of all varieties. Many prior art clamps are as simple as a pair of opposed jaws that are held together by the force of a users' hand. Other prior art clamps utilize various locking mechanisms hold the clamp jaws in place once they are appropriately positioned. However, these prior art clamps suffer from the inability to clamp two members that are displaced or spaced from one another, without the participation of multiple users to force the two members together and operate the clamp.

Accordingly, there is a need in the art for a clamp that is capable of holding two members together that include clamp jaws that are readily adjusted in three dimensions and deployed to counteract "offset" or displacement between the two members. The independent adjustment and alignment of two clamping members into relative positions presents a substantial improvement in the art.

BRIEF DESCRIPTION OF THE DRAWING FIGURES

DETAILED DESCRIPTION OF THE PREFERRED EMBODIMENT(S)

Figure 1:
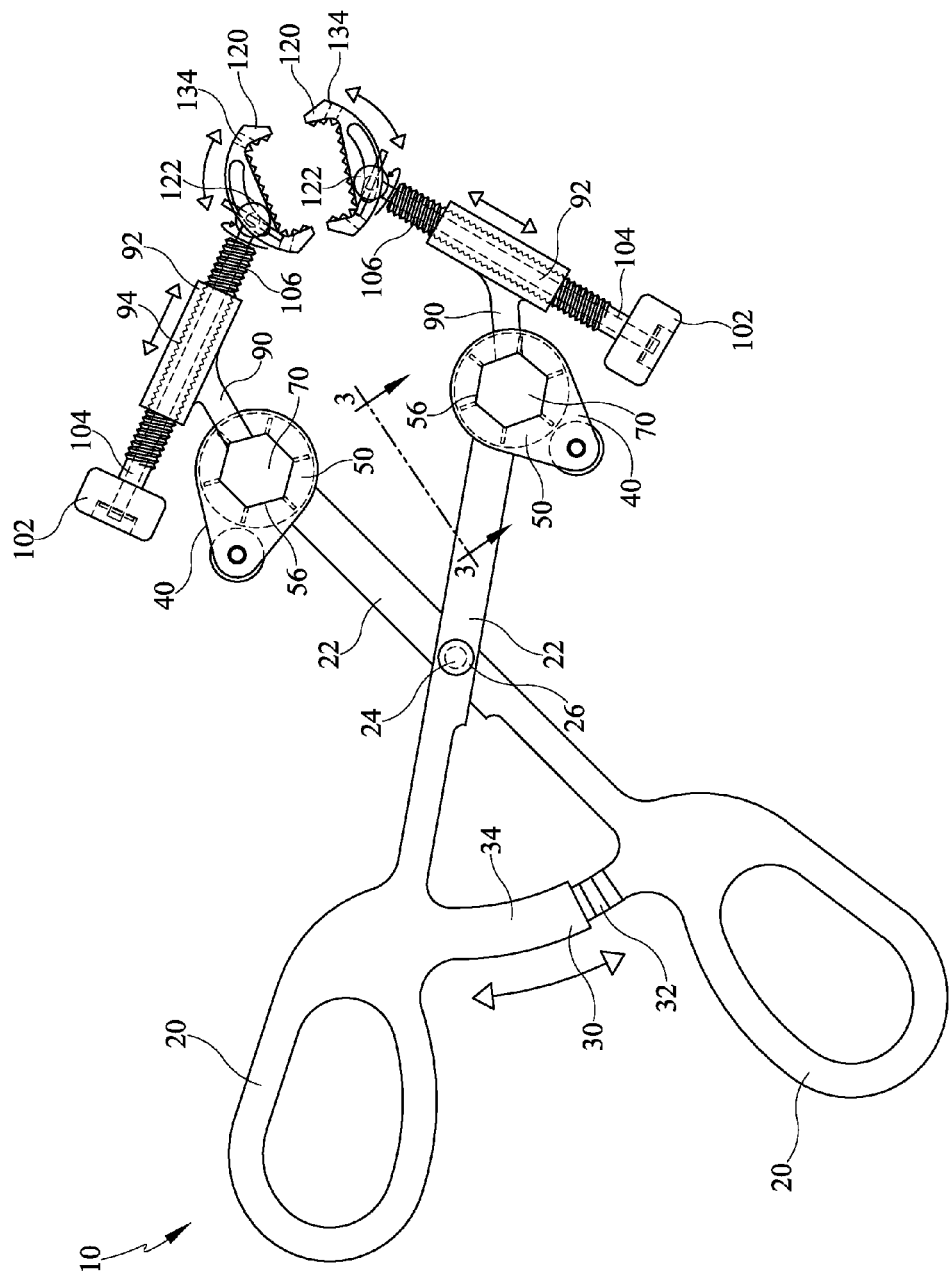
FIG. 1 is an elevation view of a clamp in accordance with one embodiment of the present invention.
Figure 2:
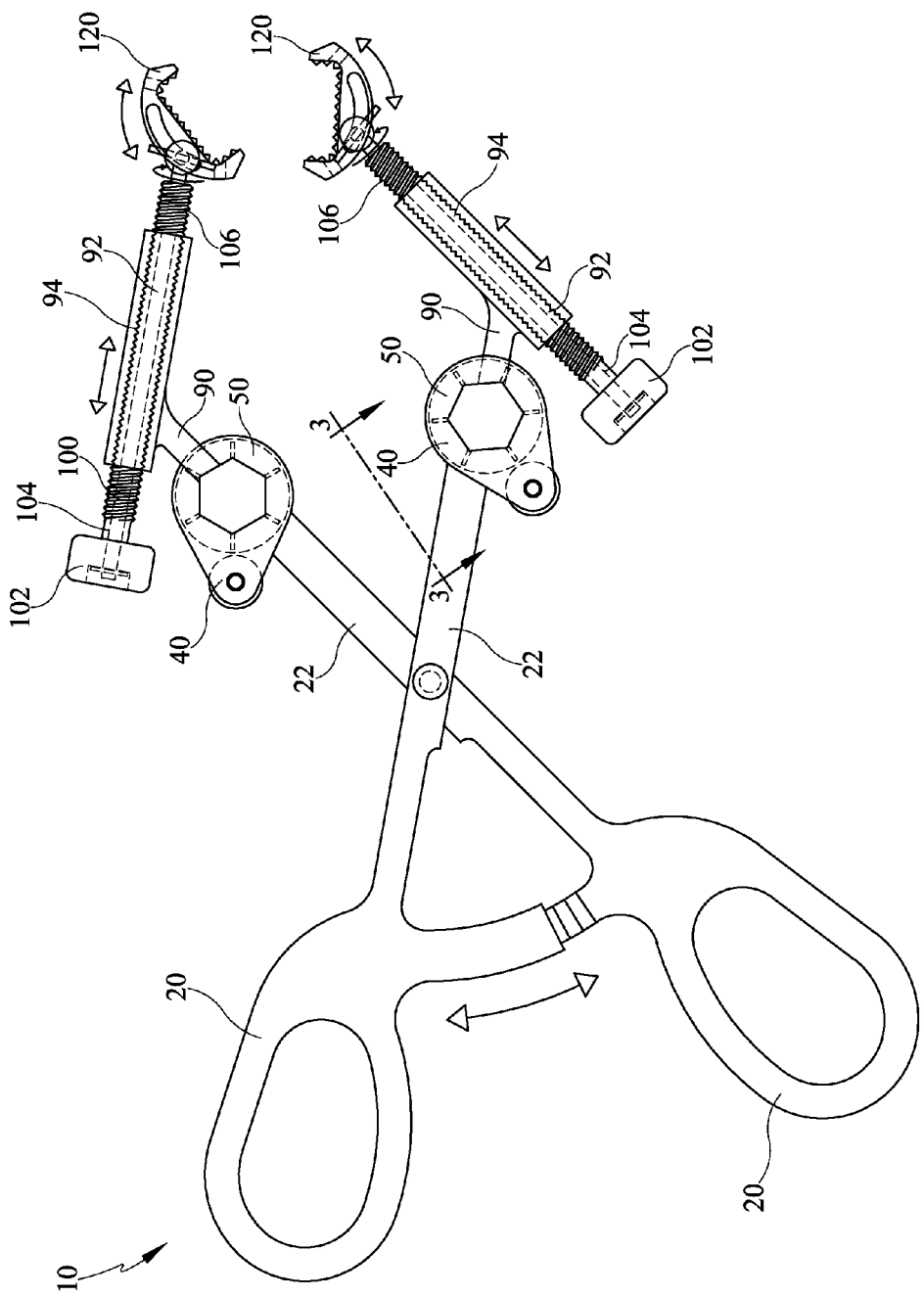
FIG. 2 is an elevation view of a clamp in accordance with one embodiment of the present invention.
Figure 3:
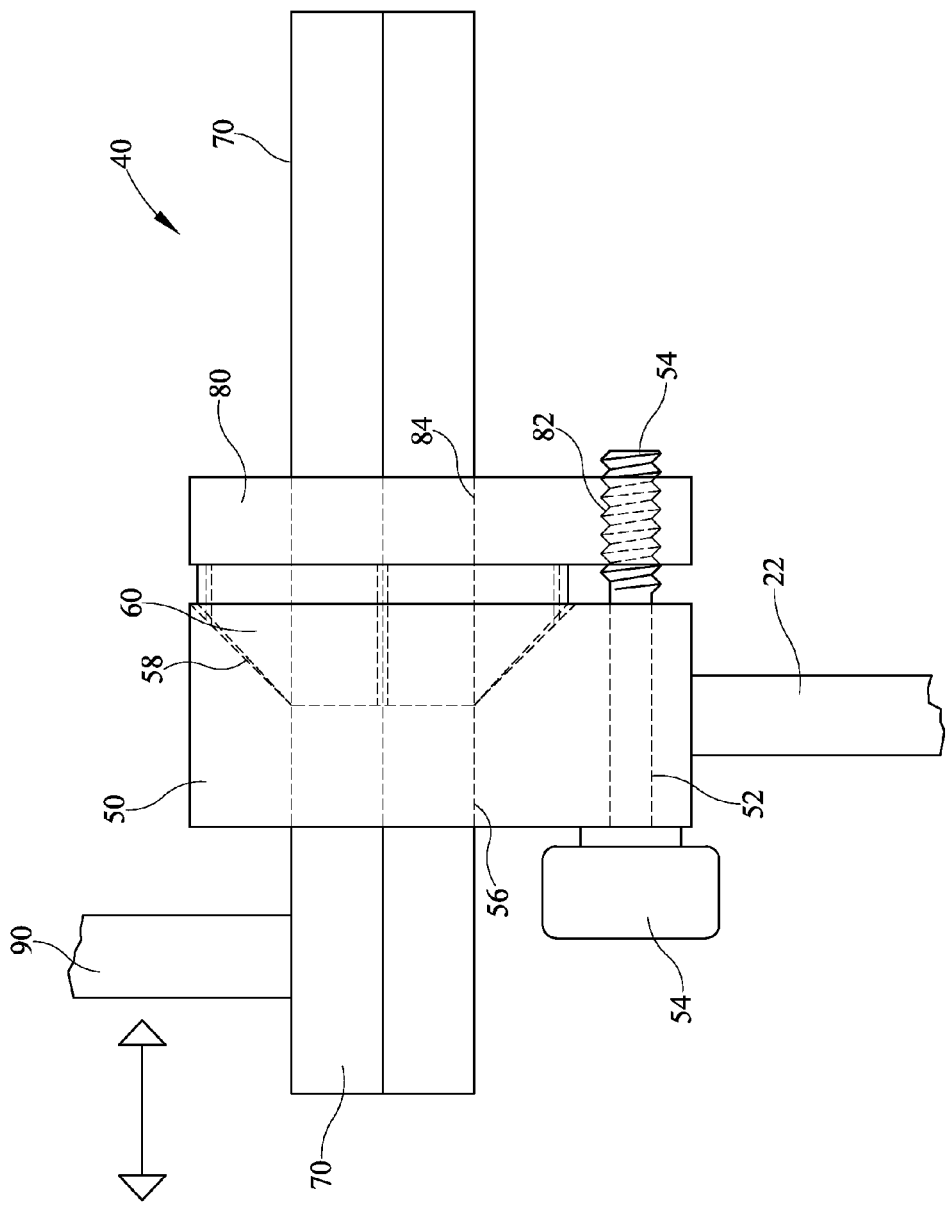
FIG. 3 is a detail view of an offset adjustment assembly taken along the line 3-3 of FIG. 1 in accordance with one embodiment of the present invention.

Referring now to drawing FIGS. 1-3, and in accordance with an exemplary embodiment of the present invention, there is depicted a clamp 10 for joining or securing two spaced members together that includes a pair of opposed handles 20 each having a central shaft 22 secured thereto. Shafts 22 are pivotally secured together at a point by a hinge 24, which may comprise a simple pin that is inserted through an aperture 26 in each shaft 22.

In one embodiment of the invention handles 20 may include a locking mechanism 30 to secure handles together in spaced relation. Locking mechanism 30 may comprise a plurality of teeth 32 arranged along a locking arm 34, that engage concomitant teeth 32 on an opposed locking arm 34 as handles 20 are moved toward each other.

Shafts 22 terminate in an offset adjustment assembly 40, depicted in detail in FIG. 3. Offset adjustment assembly 40 includes a collar 50 that is secured to shaft 22 at a point. Collar 50 comprises a first aperture 52 through which a set or clamp screw 54 is inserted, and further comprises a second aperture 56 shaped to accept an offset bar 70 there through. Second aperture 56 may include a partially conical cutout portion 58 that is shaped to engage a frusto-conical wedge 60, best seen in FIG. 3.

Offset adjustment assembly also includes a threaded plate 80 having a first threaded aperture 82 that is engaged by an end of clamp screw 54 and a second aperture 84 shaped to accept offset bar 70. By tightening clamp screw 54, threaded plate 80 forces wedge 60 into second aperture 56 cutout portion 58, thereby securing offset bar 70 in collar 50. Wedge 60 may be integral with threaded plate 80, in one embodiment of the instant invention. By loosening clamp screw 54, offset bar 70 may slide through collar 50, thereby providing a lateral offset to clamp 10, as discussed in detail herein below and shown in FIGS. 12-14. It should be noted that while offset bar 70 and second apertures 56 and 84 are depicted as generally hexagonal in shape, any shape offset bar 70 and apertures 56, 84 may be used without departing from the scope of the instant invention.

Referring again to FIGS. 1-3 offset bar 70 is secured at a point to an arm 90 that terminates in a cylindrical arm 92. Cylindrical arm 92 includes a plurality of helical threads 94 in its interior surface that engage a threaded clamp arm 100. Clamp arm 100 may include a finger grip 102 at a proximal end 104 thereof to facilitate a user rotating arm 100, thereby extending or retracting clamp arm 100 as necessary. As readily seen in FIG. 12, offset bar 70 may be slid to provide lateral spacing between clamp arms 100.

Figure 15:
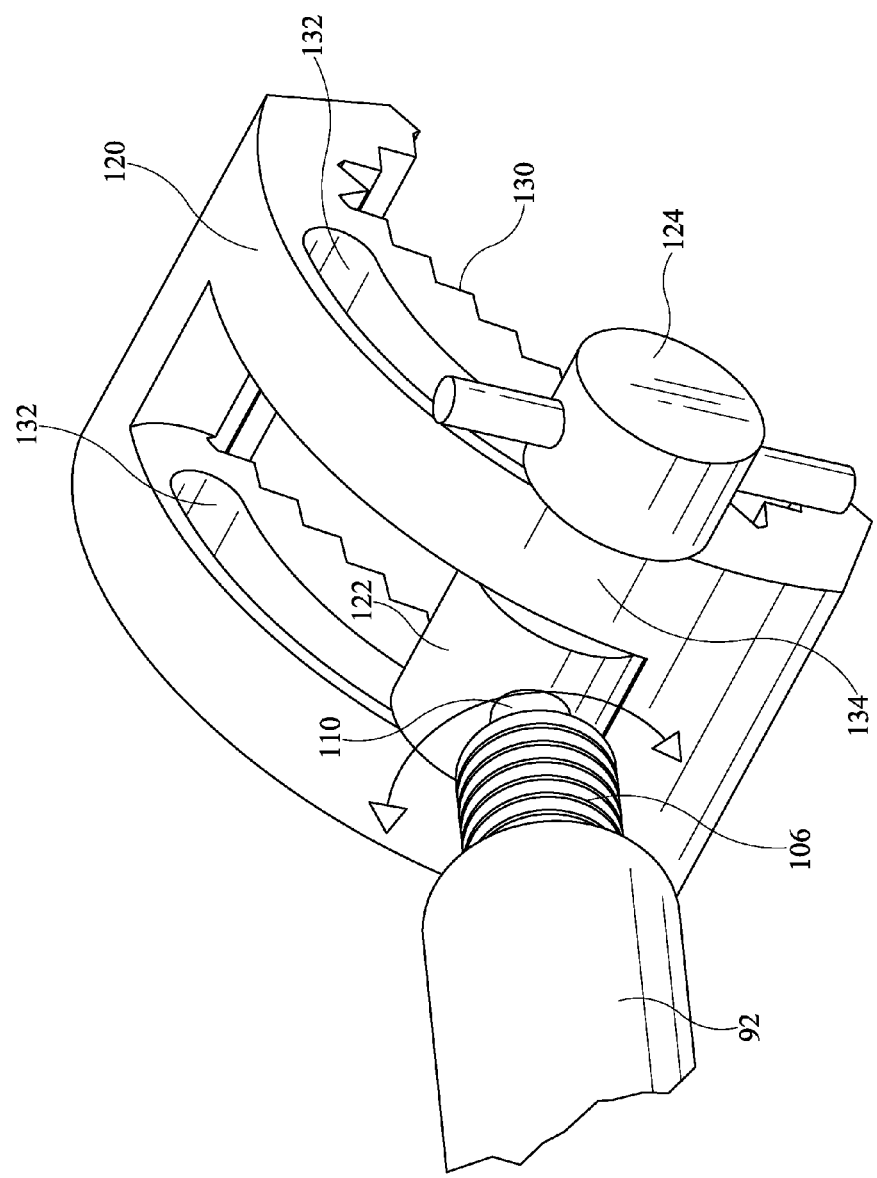
FIG. 15 is a detail view of a clamp jaw in accordance with one embodiment of the present invention.

A distal end 106 of clamp arm 100 terminates in an unthreaded portion 110, which is rotatably secured to a clamp jaw 120 retaining pin 122, as shown in detail in FIG. 15. Clamp 10 utilizes a pair of clamp jaws 120, each rotatably secured to distal end 106 of a clamp arm 100, and each having a plurality of teeth or gripping surfaces for contacting and securing a member being clamped. Clamp jaw 120 may also comprise an opposed pair of slots 132 through which retaining pin 122 may be inserted to enable a user to adjust the angle of clamp jaw 120. As depicted in the Figures, slots 132 may be generally arcuate in shape to enable rotation of clamp jaw 120. Retaining pin 122 includes a threaded cap 124 that may be tightened to secure pin 122 in slots 132, thereby prohibiting further rotation of clamp jaw 120 once it is adjusted to a users' liking.

Additionally, clamp jaws 120 may comprise an aperture 134, or a plurality thereof, that extend through clamp jaws 120 and that enable a user to secure clamp jaws 120 directly to a member being clamped by use of a fastener such as a screw. This feature of the instant invention is particularly useful in certain medical applications, such as the setting of fractured bones, since clamp jaws 120 can be secured directly to the bones to eliminate any slipping of clamp 10 as the bones are being set, and its attendant damage to soft tissue.

In an alternative embodiment of the present invention as depicted in FIG. 2, cylindrical arms 92 and clamp arms 100 are elongated to provide clamping force a greater distance from a users' hand.

Figure 4:
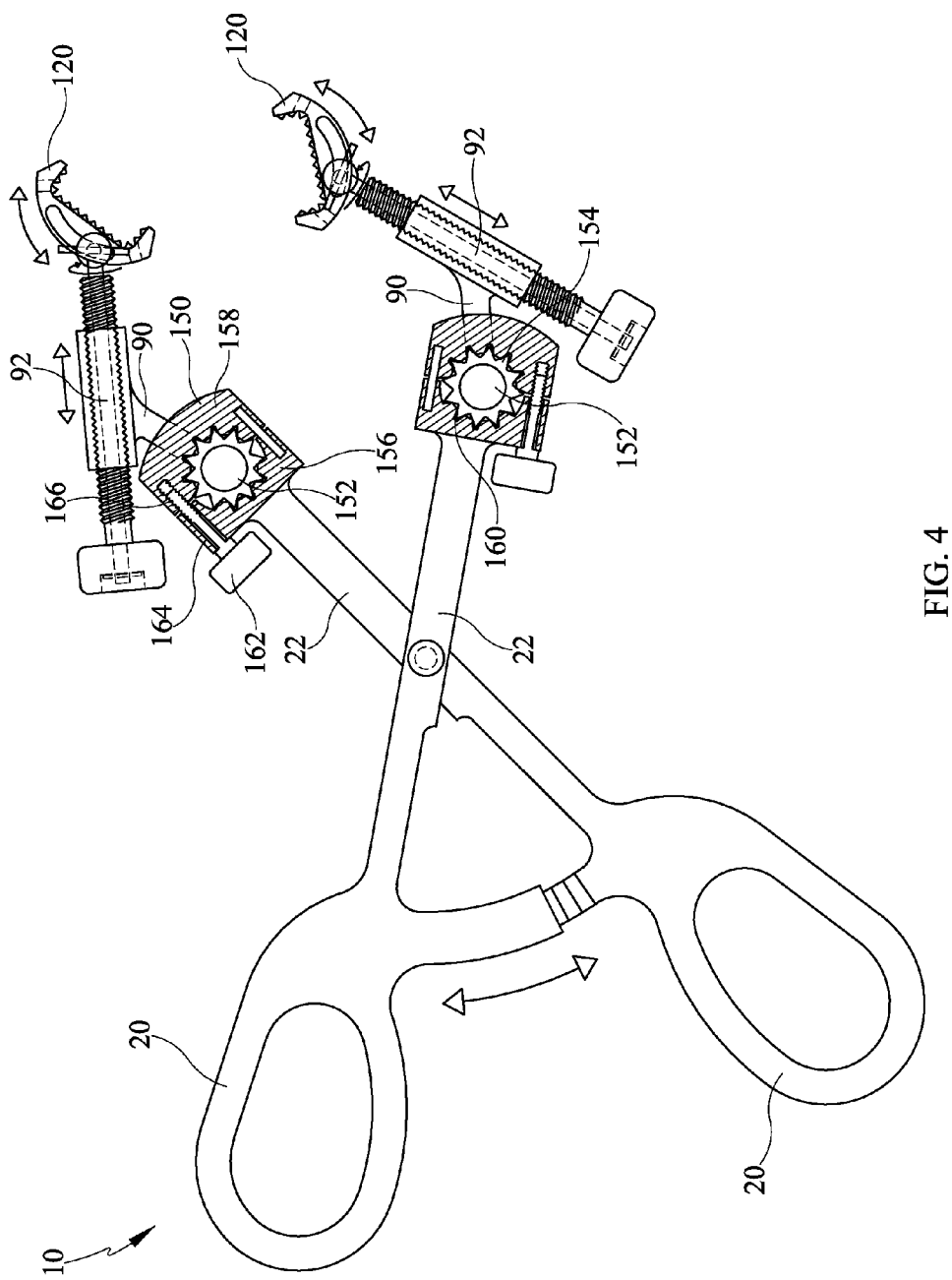
FIG. 4 is an elevation view of a clamp in accordance with one embodiment of the present invention.
Figure 5:
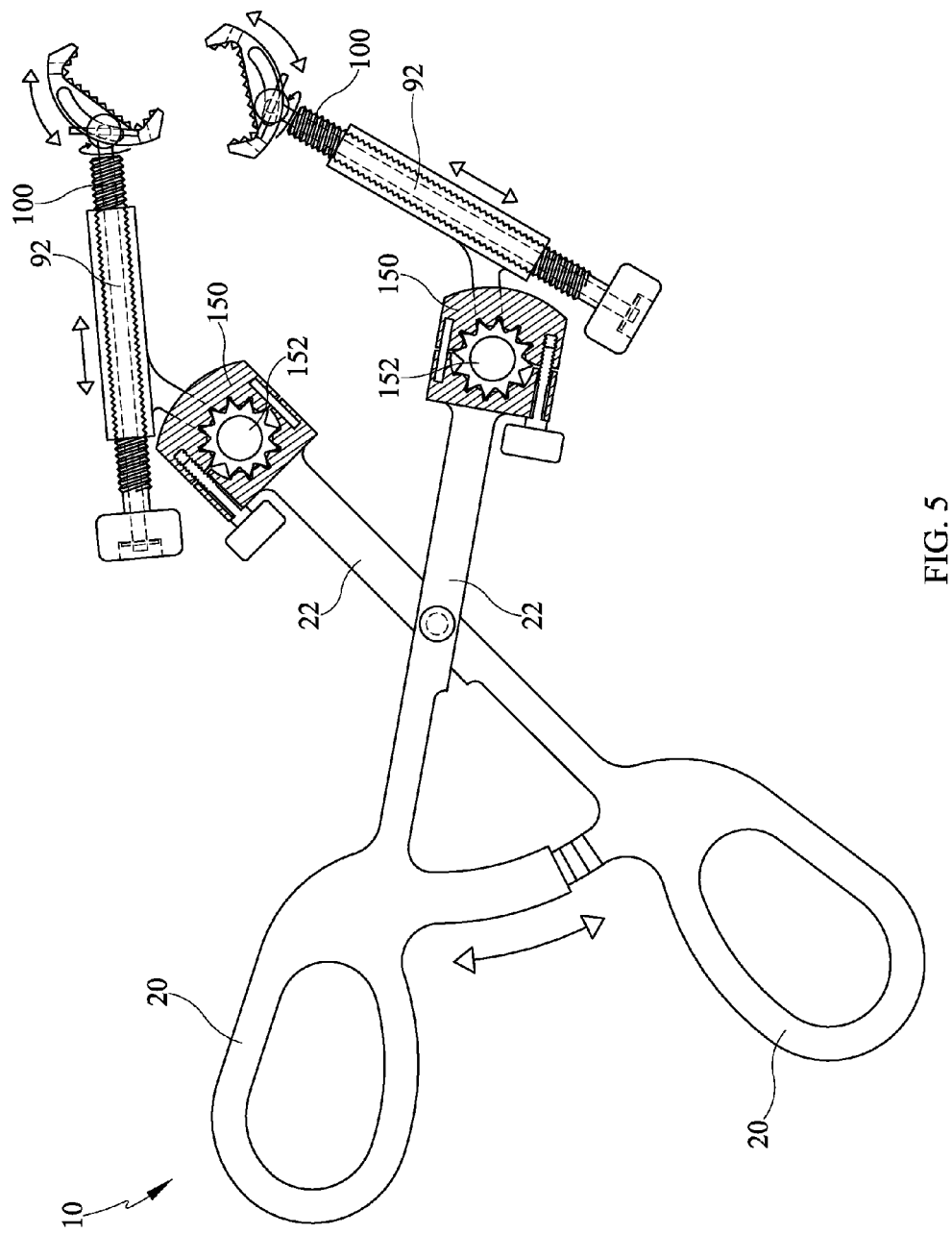
FIG. 5 is an elevation view of a clamp in accordance with one embodiment of the present invention.

In another alternative embodiment of the invention as shown in FIGS. 4 and 5 an angular adjustment assembly 150 is secured to shafts 22. Angular adjustment assembly 150 includes a ring 152 having a plurality of teeth 154 secured to its circumference, the ring being secured to arm 90 and thus to cylindrical arm 92. Angular adjustment assembly 150 may comprise a two-piece body, 156, 158 each having a plurality of notches 160 in an interior portion thereof that engage teeth 154 of ring 152. Body piece 156 is secured to shaft 22 of clamp 10, and is secured to body piece 158 by a threaded screw 162 that is inserted through an aperture 164 in piece 156 to engage a threaded aperture 166 in body piece 158. By loosening screw 162 body pieces 156 and 158 may be separated thereby freeing ring 152, which can then be rotated to any angular position desired by a user. This angular position is then maintained by tightening screw 162, thereby engaging teeth 154 with notches 160. FIG. 5 depicts an embodiment of the invention similar to that of FIG. 4, having elongated cylindrical arms 92 and clamp arms 100.

Figure 6:
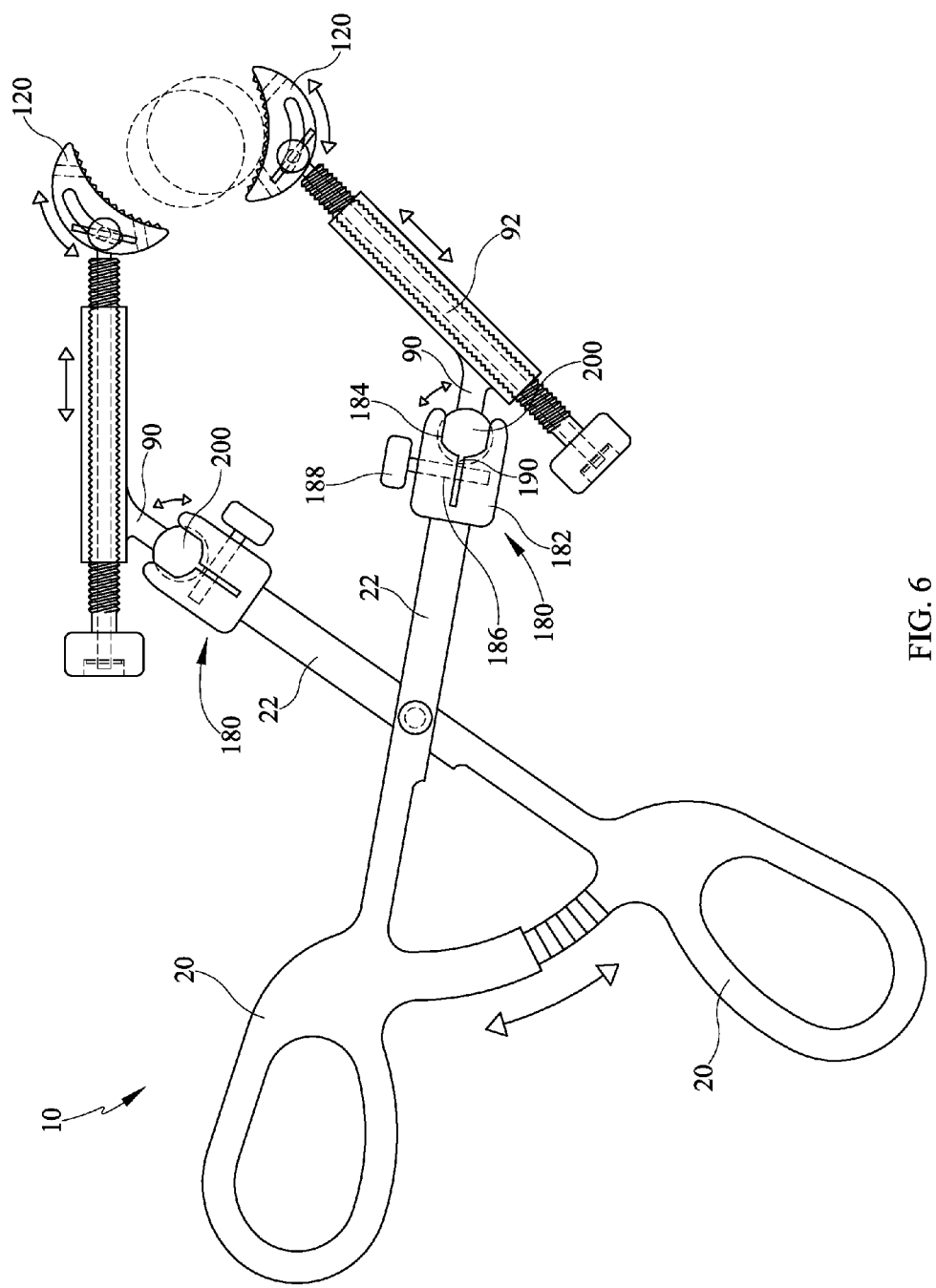
FIG. 6 is an elevation view of a clamp in accordance with one embodiment of the present invention.

Referring now to FIG. 6, and in another alternative embodiment of the instant invention, clamp 10 shafts 22 terminate in a ball joint assembly 180 that includes a ball clamp 182 having a semi-spherical notch 184 therein and a threaded aperture 186 that accepts a clamp set screw 188 there through. A central longitudinal passage 190 is also provided in clamp 182 that communicates with semi-spherical notch 184 and is bisected by set screw 188. A ball 200 is secured to arm 90, and thence to cylindrical arm 92, and is secured in semi-spherical notch 194 by tightening set screw 188. Loosening set screw 188 permits rotation of ball 200 and thereby adjustment of the position of clamp jaws 120.

Figure 7:
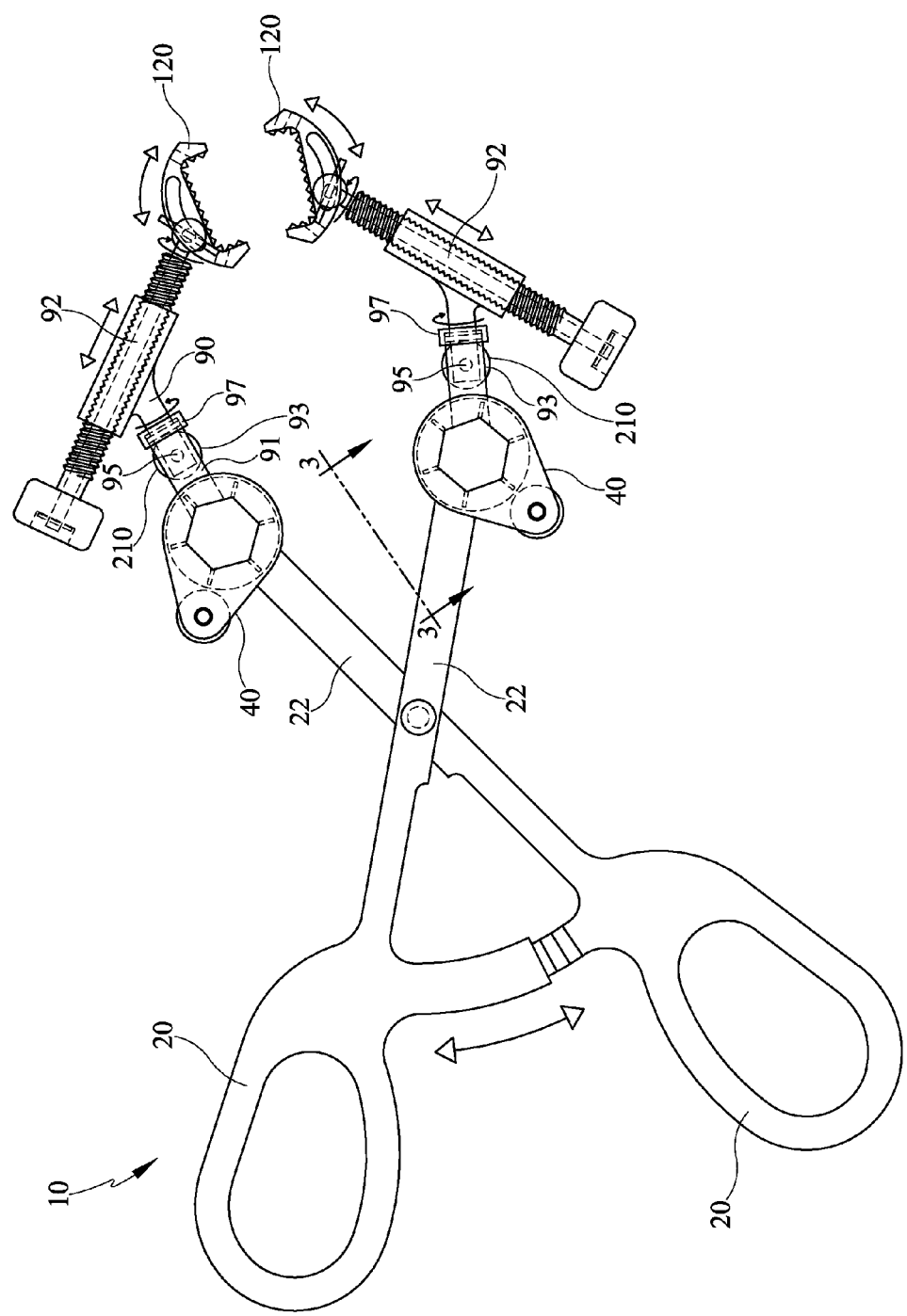
FIG. 7 is an elevation view of a clamp in accordance with one embodiment of the present invention.
Figure 8:
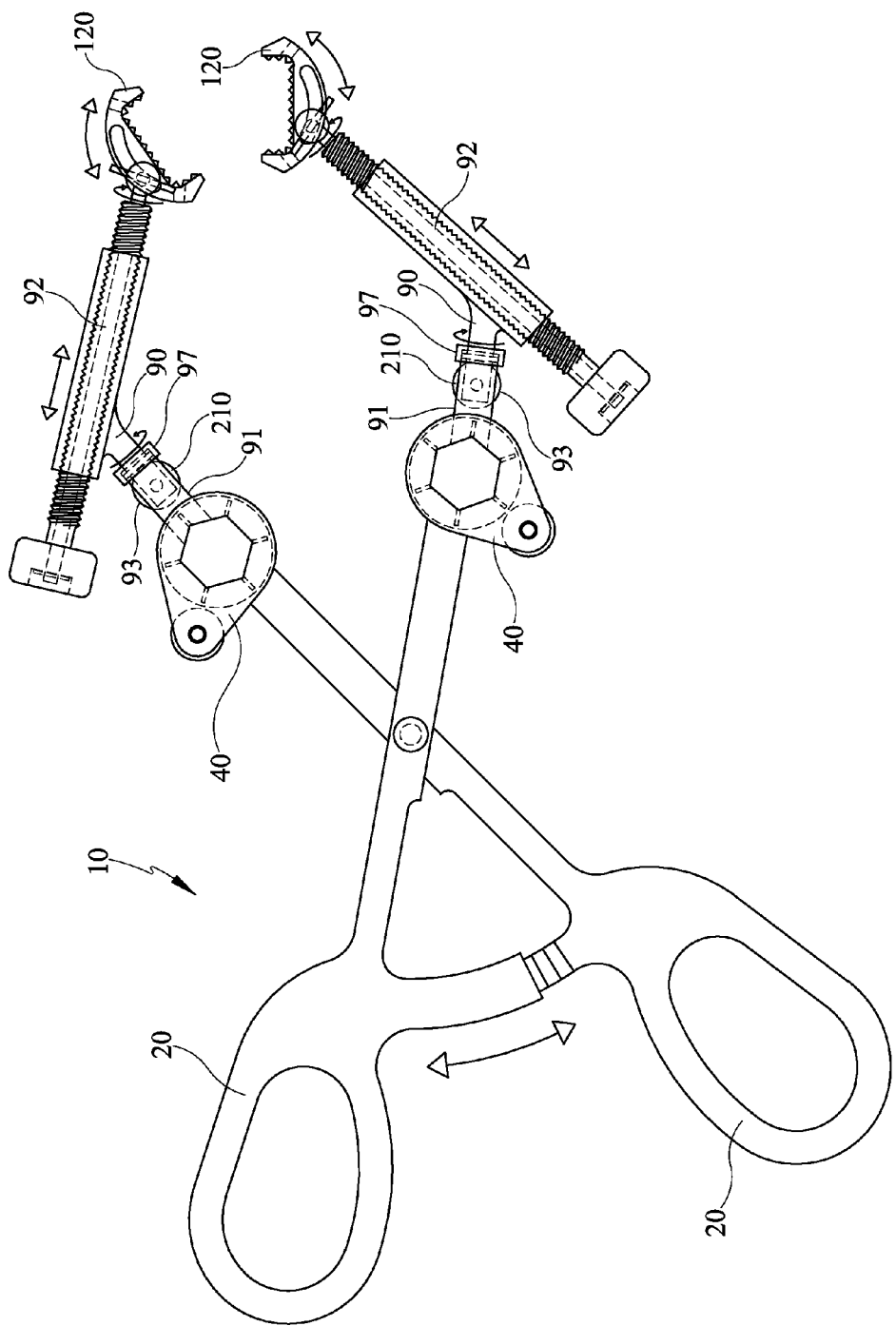
FIG. 8 is an elevation view of a clamp in accordance with one embodiment of the present invention.

In a yet further embodiment of the instant invention as depicted in FIGS. 7 and 8, an additional swivel joint assembly 210 is provided to permit rotation of clamp jaws 120. In this embodiment of the invention, arm 90 comprises a tube that has a slightly smaller diameter than that of a swivel tube 91 that is secured to lateral adjustment assembly 40. Arm 90 is inserted into swivel tube 91 and is retained in its position by a set screw 93 that is threaded through an aperture 95 in swivel tube 91. When set screw 93 is loosened, arm 90 is free to rotate into a desired position. Set screw 93 can then be tightened to secure arm 90, and thus clamp jaws 120, in position. In one embodiment of the invention a collar 97 is provided that engages both arm 90 and swivel tube 91 and permits them to slide relative to each other, but does not permit arm 90 to completely disengage swivel tube 91. FIG. 8 depicts an embodiment of the invention similar to that of FIG. 7, having elongated cylindrical arms 92 and clamp arms 100.

Figure 9:
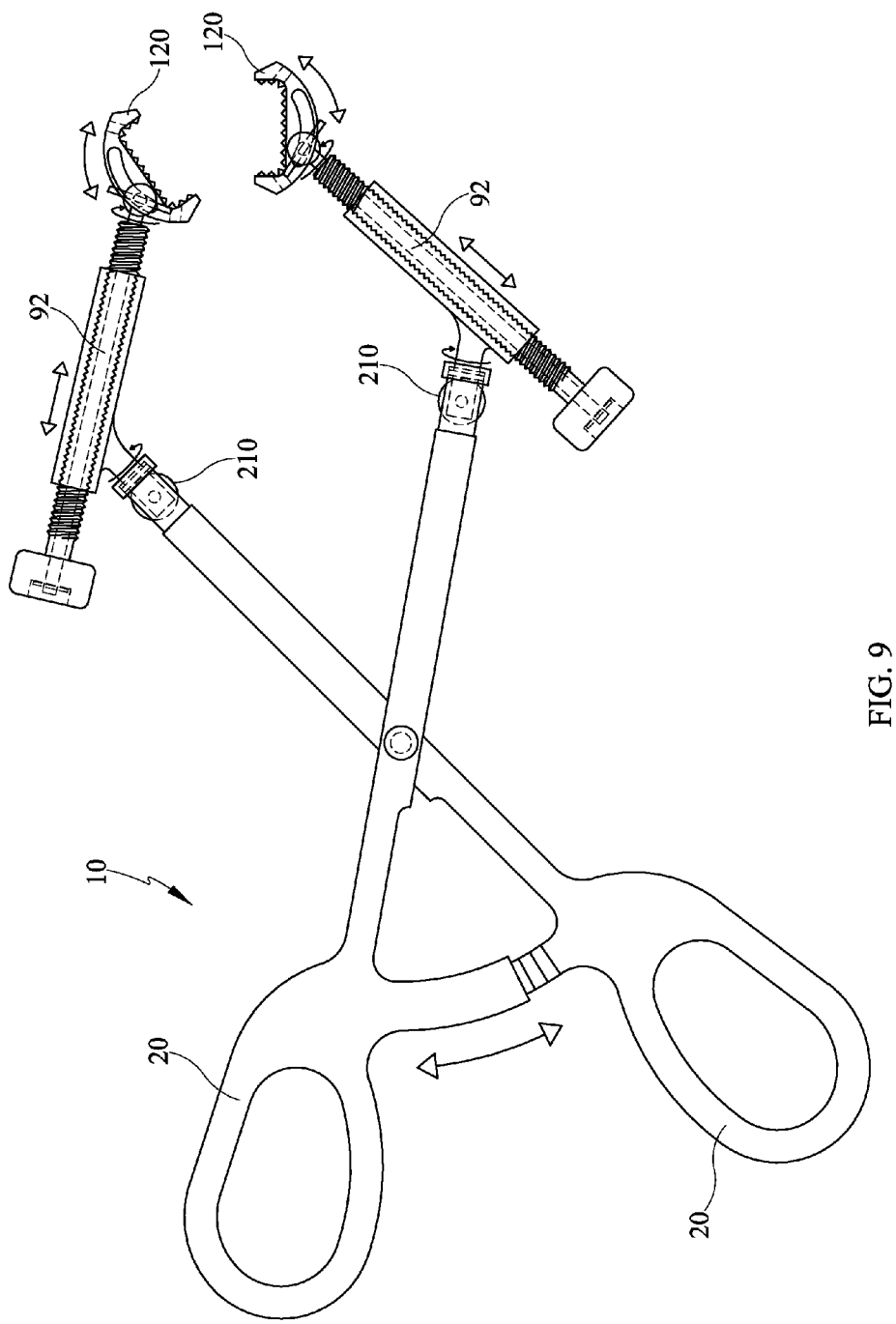
FIG. 9 is an elevation view of a clamp in accordance with one embodiment of the present invention.
Figure 10:
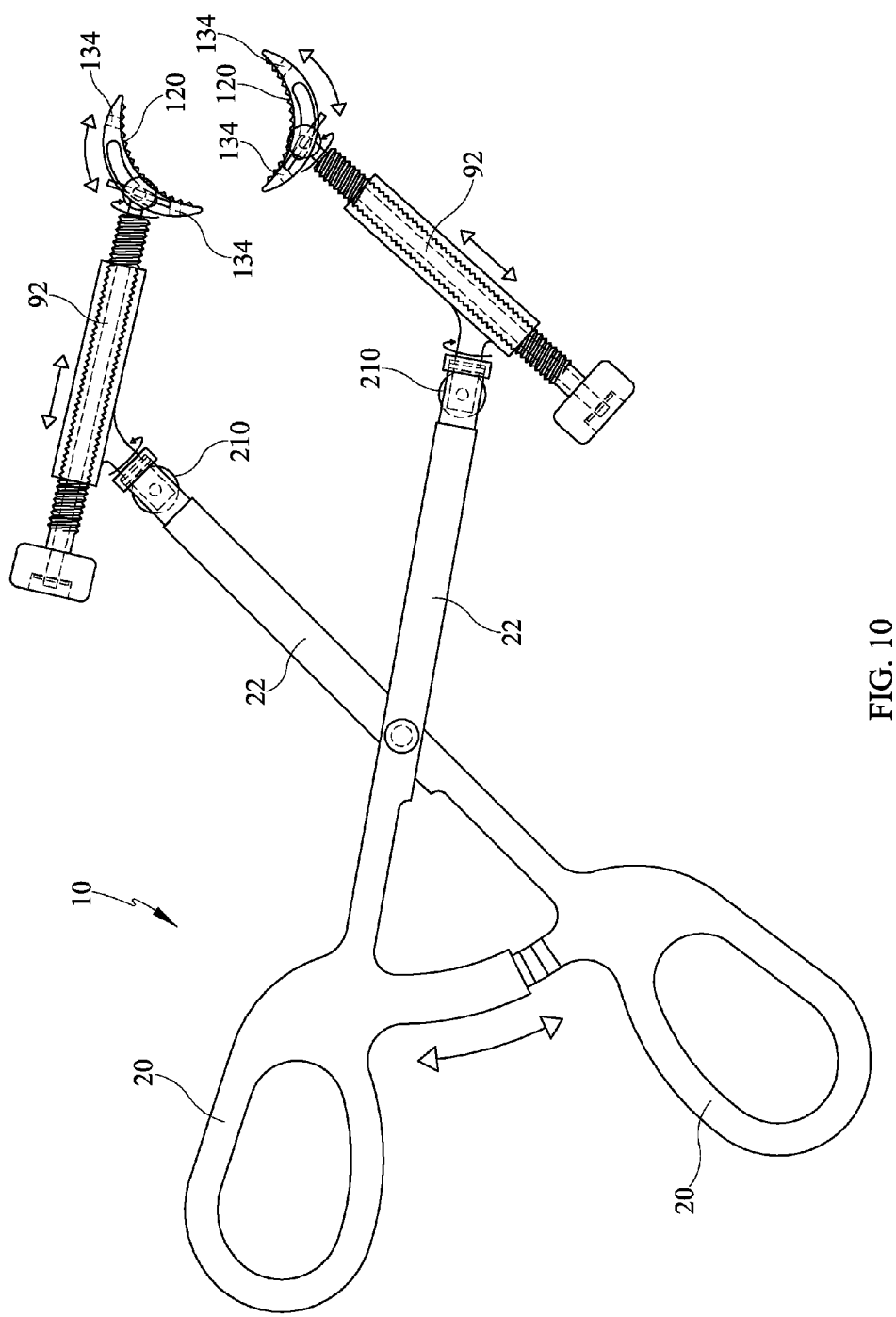
FIG. 10 is an elevation view of a clamp in accordance with one embodiment of the present invention.

Referring now to FIGS. 9 and 10, clamp 10 comprises an additional embodiment wherein shafts 22 are secured directly to swivel joint 210. This embodiment of the invention provides a simple and economical clamp 10 that still retains flexibility in use. FIG. 10 depicts an embodiment of the invention similar to that of FIG. 9, with the exception of the use of crescent-shaped clamp jaws 102, which may be more suitable for use in situations where relatively cylindrical members are being joined.

Figure 11:
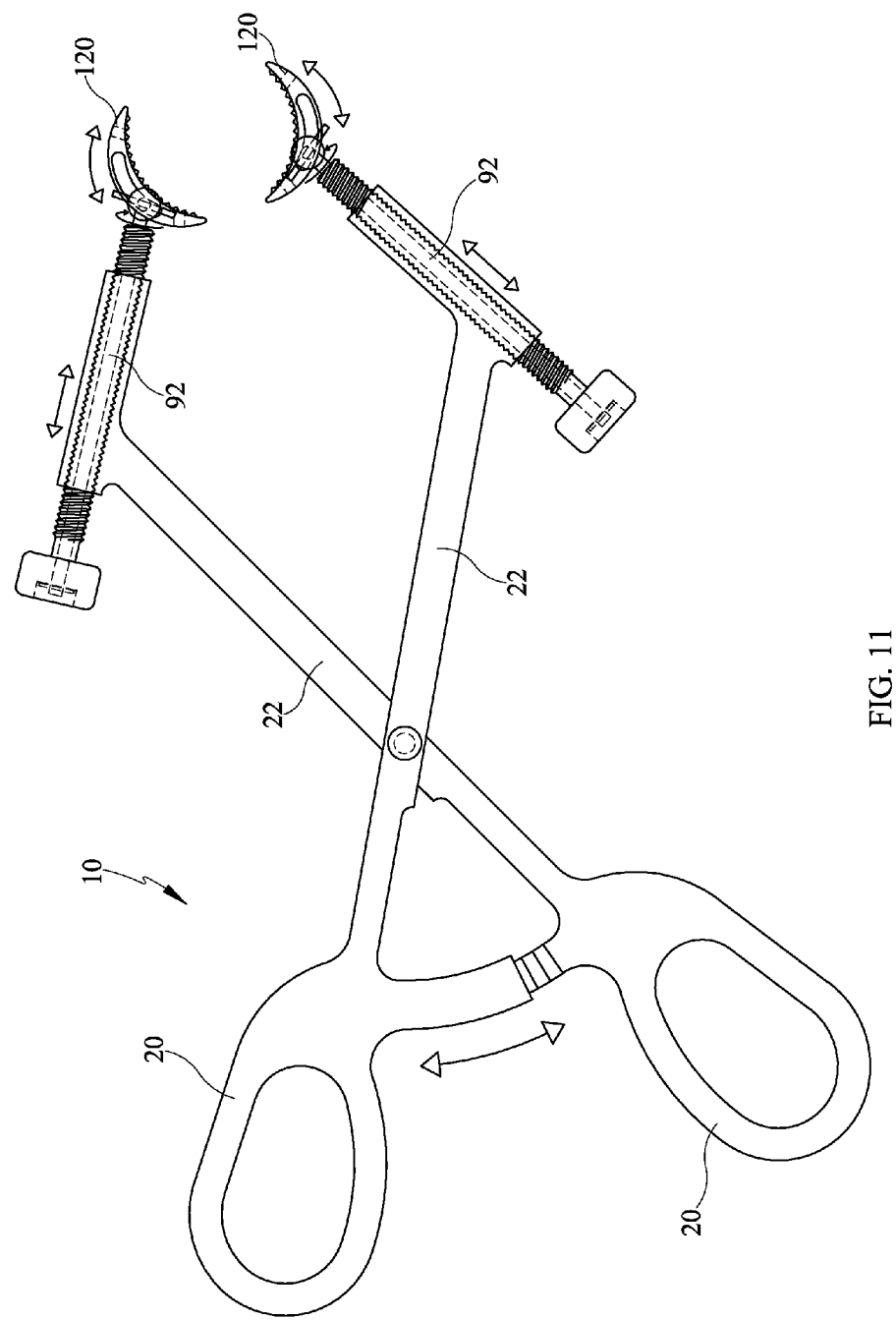
FIG. 11 is an elevation view of a clamp in accordance with one embodiment of the present invention.

FIG. 11 depicts an alternative embodiment of the invention wherein shafts 22 are secured directly to cylindrical arms 92. This embodiment of the invention is economical to manufacture, and still enables the user to adjust the both the angle and extension of clamp jaws 102 quickly and efficiently.

Figure 12:
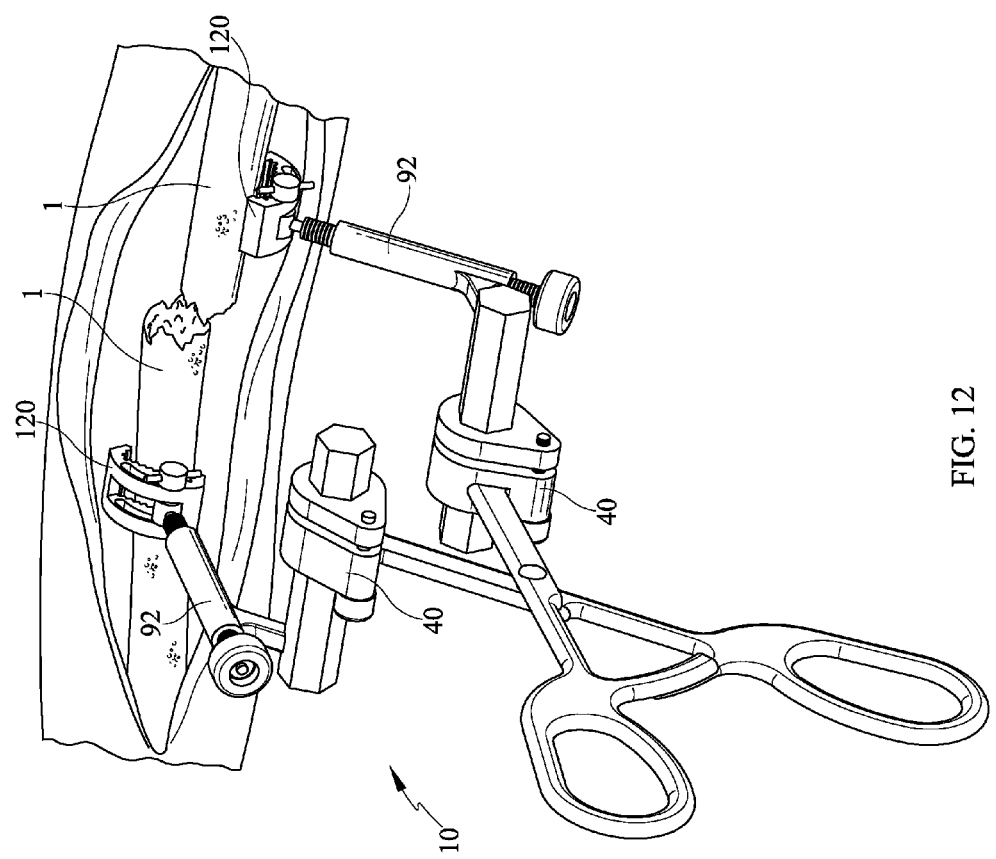
FIG. 12 is an isometric view of a clamp being used to set a bone fracture in accordance with one embodiment of the present invention.
Figure 13:
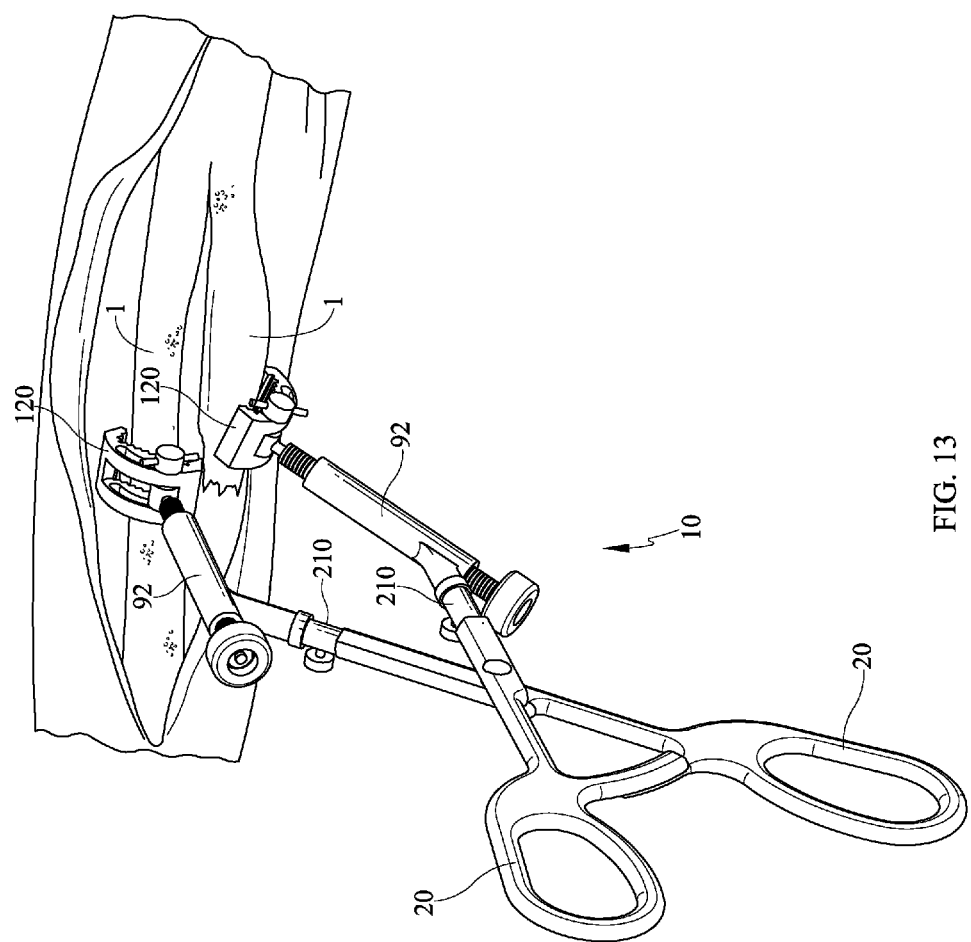
FIG. 13 is an isometric view of a clamp being used to set a bone fracture in accordance with one embodiment of the present invention.
Figure 14:
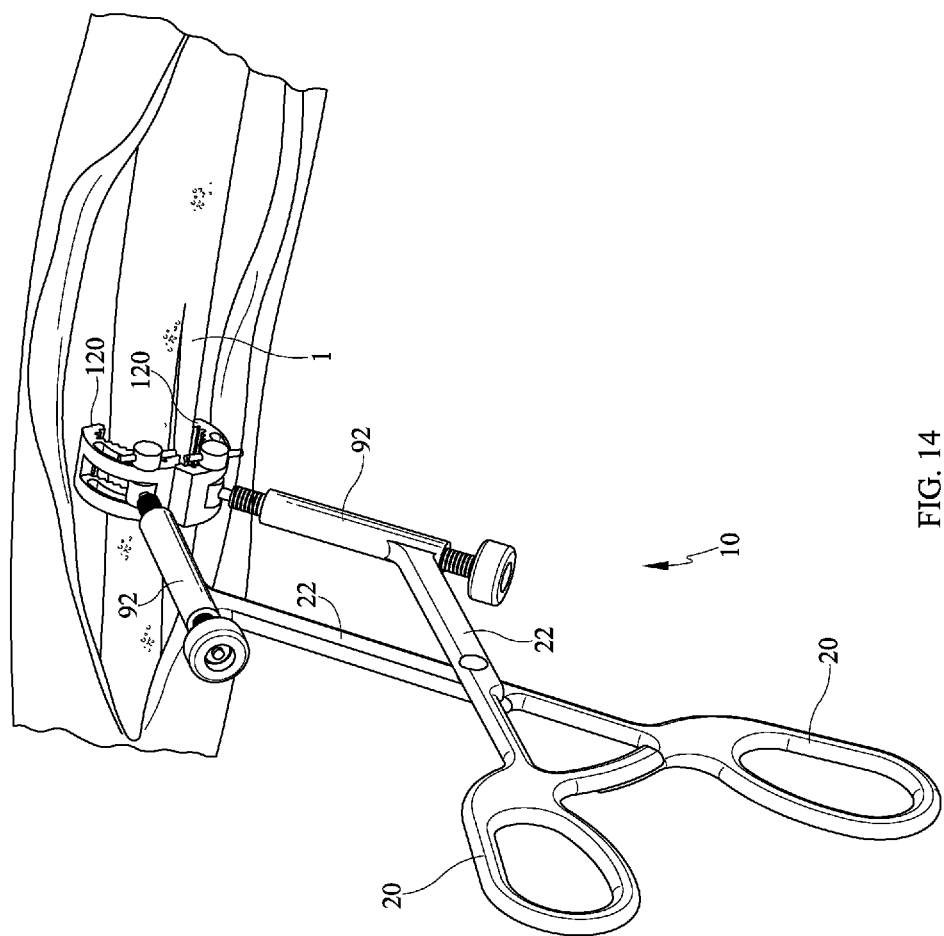
FIG. 14 is an isometric view of a clamp being used to set a bone fracture in accordance with one embodiment of the present invention.

Referring now to FIG. 12, clamp 10 is depicted employed in clamping two members 1, the members in this exemplary embodiment being a fractured bone. Offset assembly 40 is employed to move clamp jaws 120 laterally apart to facilitate setting the bone. FIGS. 13 and 14 also depict alternative embodiments of the instant invention discussed herein above employed in setting or clamping a fractured bone 1. It will be appreciated by one of ordinary skill in the art that the various embodiments of the invention described and claimed herein provide a highly configurable and adjustable clamp that facilitates securing two members efficiently by a single user.

While the present invention has been shown and described herein in what are considered to be the preferred embodiments thereof, illustrating the results and advantages over the prior art obtained through the present invention, the invention is not limited to those specific embodiments. Thus, the forms of the invention shown and described herein are to be taken as illustrative only and other embodiments may be selected without departing from the scope of the present invention, as set forth in the claims appended hereto.

We claim:

1. An apparatus for providing a clamping force to two objects to be clamped together comprising:
    a pair of opposed handles, each of said handles having a shaft secured thereto, said shafts pivotally secured together at a central point;
    an offset adjustment assembly secured to each shaft at a terminal end thereof, said offset adjustment assembly including a collar secured to said shaft, said collar having an aperture therein and an offset bar slidably engaged for lateral motion through said collar aperture, said offset bar secured to said cylindrical arm;
    a cylindrical arm secured to each adjustment assembly, said cylindrical arm having an aperture therein;
    an extendable arm disposed through the aperture of each of said cylindrical arms and having distal and proximal ends, said extendable arm capable of being extended and retracted through said aperture; and
    a clamp jaw pivotally secured to each of said extendable arms, whereby forcing said handles together forces said clamp jaws together.

2. An apparatus as claimed in claim 1 comprising:
    a frusto-conical surface disposed in the aperture of said collar; and
    a frusto-conical wedge engaging the frusto-conical surface of said collar to prohibit lateral motion of said offset bar through said collar aperture.

3. An apparatus as claimed in claim 1 wherein said offset adjustment assembly comprises an angular adjustment assembly comprising:

a body having first and second pieces secured together by a releasable fastener, each having a plurality of notches at an interior portion thereof, said first body piece secured to said shaft; and a ring having a plurality of teeth on the circumference thereof, said ring secured to said cylindrical arm.

4. An apparatus as claimed in claim 1 wherein said offset adjustment assembly comprises a ball joint assembly comprising:

a ball clamp secured to said shaft, said clamp having a semi-spherical notch therein bisected by a clamp screw for compressing said notch;

a spherical ball secured to said cylindrical arm, said ball secured in said notch wherein the tightening of said clamp screw prevents said ball from rotation in said ball clamp.

* * * * *